(12) United States Patent
Takanashi et al.

(10) Patent No.: US 11,434,376 B2
(45) Date of Patent: Sep. 6, 2022

(54) AMINOCOUMARIN COMPOUND, AND AMINOCOUMARIN COMPOUND-CONTAINING RESIN PARTICLES

(71) Applicant: Konica Minolta, Inc., Tokyo (JP)

(72) Inventors: Kensaku Takanashi, Hino (JP); Shin Nakayama, Hino (JP); Kenji Nishikawa, Hino (JP); Takeshi Isoda, Sayama (JP)

(73) Assignee: KONICA MINOLTA, INC., Tokyo (JP)

( * ) Notice: Subject to any disclaimer, the term of this patent is extended or adjusted under 35 U.S.C. 154(b) by 585 days.

(21) Appl. No.: 16/477,433

(22) PCT Filed: Feb. 13, 2018

(86) PCT No.: PCT/JP2018/004803
§ 371 (c)(1),
(2) Date: Jul. 11, 2019

(87) PCT Pub. No.: WO2018/151072
PCT Pub. Date: Aug. 23, 2018

(65) Prior Publication Data
US 2021/0277250 A1 Sep. 9, 2021

(30) Foreign Application Priority Data

Feb. 14, 2017 (JP) .............................. JP2017-024875
Feb. 14, 2017 (WO) ................... PCT/JP2017/005284

(51) Int. Cl.
C09B 57/02 (2006.01)
C08K 5/1545 (2006.01)

(52) U.S. Cl.
CPC ............ *C09B 57/02* (2013.01); *C08K 5/1545* (2013.01)

(58) Field of Classification Search
CPC .................................................... C09B 57/02
USPC ..................................................... 252/301.3
See application file for complete search history.

(56) References Cited

FOREIGN PATENT DOCUMENTS

| EP | 3059775 A1 * | 8/2016 | .......... C07C 211/54 |
|---|---|---|---|
| JP | H06-9892 A | 1/1994 | |
| JP | H06-271599 A | 9/1994 | |
| JP | 07-508309 A | 9/1995 | |
| JP | 2004309458 A | 11/2004 | |
| JP | 2006045314 A | 2/2006 | |
| JP | 2013227552 A | 11/2013 | |
| JP | 2015-093878 A | 5/2015 | |
| JP | 2015108572 A | 6/2015 | |
| WO | 2014/192972 A1 | 12/2014 | |
| WO | 2015041157 A1 | 3/2015 | |
| WO | WO-2015041157 A1 * | 3/2015 | .......... C07C 211/54 |
| WO | 2015/045961 A1 | 4/2015 | |
| WO | 2016/129444 A1 | 8/2016 | |

OTHER PUBLICATIONS

JPO, Office Action for the corresponding Japanese patent application No. 2018-568516, dated Nov. 2, 2021, with English translation.
JPO, Office Action for the corresponding Japanese patent application No. 2018-568515, dated Jan. 18, 2022, with English translation.
JPO, Office Action for the corresponding Japanese patent application No. 2018-568515, dated Jul. 13, 2021, with English translation.
PCT, International Search Report for the corresponding application No. PCT/JP2018/004803, dated May 1, 2018, with English translation (7 pages).
PCT, Written Opinion of the International Searching Authority for the corresponding application No. PCT/JP2018/004803, dated May 1, 2018, with English translation (10 pages).
Karel Goossens et al. , "Accurate Diffusion Coefficients of Organosoluble Reference Dyes in Organic Media Measured by Dual-Focus Fluorescence Correlation Spectroscopy," ACS NANO, 2015, pp. 7360-7373, vol. 9, No. 7.
Hyosung Jung et al., "Rationally DesignedFluorescence Turn-On Sensors: A New Design Strategy Based on Orbital Control," Inorganic Chemistry, 2010, pp. 8552-8557, vol. 49.
Kensuke Komatsu et al., "Development of an Iminocoumarin-Based Zinc Sensor Suitable for Ratiometric Fluorescence Imaging of Neuronal Zinc," Journal of the American Chemical Society, 2007, pp. 13447-13454, vol. 129.
EPO, Extended European Search Report for the corresponding European patent application No. 18754496.0, dated Feb. 7, 2020.
JPO, Office Action for the corresponding Japanese patent application No. 2018-568516, dated Apr. 26, 2022 with English translation.

* cited by examiner

*Primary Examiner* — Deve V Hall
(74) *Attorney, Agent, or Firm* — Lucas & Mercanti, LLP (57) ABSTRACT

The present invention provides: an aminocoumarin compound having a structure represented by the following formula (1); and an aminocoumarin compound-containing resin particle containing the aminocoumarin compound and a resin particle containing the aminocoumarin compound. In formula (1), Rs each independently represent a hydrogen atom or a methyl group, Q represents a sulfur atom, an oxygen atom, or N—$R^1$, and $R^1$ represents a hydrogen atom or a methyl group. The aminocoumarin compound of the present invention is a fluorescent dye that has a longer excitation wavelength than a conventionally known sulfonated coumarin-based compound and is effectively excited at a wavelength of 475 nm or more, particularly at a wavelength around 500 nm. The aminocoumarin compound of the present invention is a fluorescent dye that is excited, for example, at a wavelength of 475 to 510 nm and can be observed in a green light emission region of 510 to 540 nm using the wavelength characteristic, and can be expected to be suitably utilized in immunostaining or the like.

8 Claims, 2 Drawing Sheets

*Fig. 1*

[Table 2]

| Evaluation item | | Example 7 | Example 8 | Example 9 | Example 10 | Example 11 | Example 12 |
|---|---|---|---|---|---|---|---|
| Particle performance | Average diameter (nm) | 150 | 150 | 133 | 134 | 132 | 133 |
| | Dye contained | Aminocoumarin compound I | Aminocoumarin compound II | Aminocoumarin compound III | Aminocoumarin compound IV | Aminocoumarin compound V | Aminocoumarin compound VI |
| | Fluorescence intensity | 630 | 620 | 400 | 450 | 460 | 500 |
| | Excitation spectrum maximum wavelength (nm) | 490 | 495 | 480 | 483 | 490 | 490 |
| | Fluorescence spectrum maximum wavelength (nm) | 535 | 536 | 522 | 523 | 535 | 535 |
| | FACS (histogram) | | | | Not measured | Not measured | |
| | FISH (number of bright spots) | 45 | 45 | 44 | 50 | 45 | 44 |

Fig. 2

[Table 3]

| Evaluation item | | Comparative Example 5 | Comparative Example 6 | Comparative Example 7 | Comparative Example 8 |
|---|---|---|---|---|---|
| Particle performance | Average diameter (nm) | 125 | 128 | 133 | 132 |
| | Fluorescence intensity | 180 | 250 | 80 | 200 |
| | Dye contained | Aminocoumarin compound i | Aminocoumarin compound ii | Aminocoumarin compound iii | Aminocoumarin compound iv |
| | Excitation spectrum maximum wavelength (nm) | 455 | 475 | 465 | 475 |
| | Fluorescence spectrum maximum wavelength (nm) | 515 | 520 | 510 | 520 |
| | FACS | Histogram having peak around fluorescence intensity of 90 | | | |
| | FISH (number of bright spots) | 11 | 6 | 18 | 9 |

AMINOCOUMARIN COMPOUND, AND AMINOCOUMARIN COMPOUND-CONTAINING RESIN PARTICLES

CROSS REFERENCE TO RELATED APPLICATION

This Application is a 371 of PCT/JP2018/004803 filed on Feb. 13, 2018 which, in turn, claimed the priority of Japanese Patent Application No. PCT/JP2017/005284 filed on Feb. 14, 2017 and Japanese Patent Application No. 2017-024875 filed on Feb. 14, 2017, all applications are incorporated herein by reference.

TECHNICAL FIELD

The present invention relates to an aminocoumarin compound that is a novel dye and an aminocoumarin compound-containing resin particle in which the aminocoumarin compound is contained in a resin.

BACKGROUND ART

In a current medical environment, in order to provide data to determine whether or not a subject is suffering from a target disease or to provide an indicator of whether a subject should be dosed, various clinical test drugs and laboratory test drugs have been developed and are a great help for treatment.

By collecting a sample such as blood or a tissue section from a subject, and detecting, identifying, and quantifying a specific target (such as a low molecular weight compound, a protein, a gene, or a cell) using an immune reaction in many cases, various tests have been developed. For example, by specifically bonding a fluorescently labeled antibody to a molecule (antigen) in a living body that increases or decreases an expression level thereof depending on whether a subject is suffering from a disease, the antigen is fluorescently labeled, and the amount of an antigen related to the disease is determined quantitatively from the amount of a fluorescent signal.

As an example of a recent clinical test drug developed in order to provide an indicator of whether an adult T-cell leukemia (ATL) patient should be dosed, a test for detecting CCR4 which is a target is obligatory before administration of an anti-CCR4 antibody mogamulizumab molecule targeting drug. For the detection of CCR4, a FACS method for causing an immune reaction in a collected blood sample and an IHC method for causing an immune reaction in a collected tissue sample have been developed. The former quantifies (scores) CCR4 by fluorescence detection, and the latter quantitates (scores) CCR4 by chromogenic detection.

By the way, also in the immunohistochemical method for causing an immune reaction in a collected tissue sample, a technique of bonding a fluorescently labeled antibody to an antigen is also known. A technique of directly or indirectly bonding an antibody to a nanoparticle containing a fluorescent dye and bonding the antibody to an antigen is considered to be useful for achieving high sensitivity.

Medical personnel strongly need to obtain a large amount of information at one time not only for the immunohistochemical method, and many methods for simultaneously detecting different targets with a plurality of fluorescent dyes are also being developed. For example, it is possible in principle to prepare a dye that emits fluorescence in each of a green region, a red region, an orange region, and a far infrared region and to detect four types of targets by an ELISA method, a FISH method, or the like in addition to the FACS method using an immune reaction, and commercialization has also been achieved.

As a dye that emits light in the green region, a sulfonated coumarin-based dye is known. Examples of the sulfonated coumarin dye include a sulfonated coumarin dye described in Patent Literature 1. The sulfonated coumarin dye has excellent solubility in water, and is therefore adaptable to fluorescence detection tools based on various immune reactions. However, meanwhile, as described below, a fluorescence noise derived from a sample has been a major factor that makes fluorescence detection and quantification inaccurate.

For example, in a case of a dye that exhibits green fluorescence, most of sulfonated coumarin dyes have an excitation spectrum maximum wavelength in a wavelength range of 470 nm or less, and significantly reduce excitation light absorption at a wavelength of 475 nm or more. For this reason, a conventional sulfonated coumarin dye is largely restricted. For example, the conventional sulfonated coumarin-based dye is affected by a wavelength range of another fluorescent dye when multiple staining is performed.

In a wavelength range shorter than 475 nm, fluorescence caused by a substance (contaminant) other than the fluorescent dye, that is, so-called auto-fluorescence tends to increase. For this reason, in immunofluorescence detection using the conventional sulfonated coumarin dye, a background fluorescence intensity is relatively high with respect to a fluorescence intensity based on a fluorescent dye, and a signal/background ratio (S/B) is low disadvantageously.

CITATION LIST

Patent Literature

Patent Literature 1: JP 6-271599 A

SUMMARY OF INVENTION

Technical Problem

The present invention is intended to solve the problems associated with related art as described above, and an object of the present invention is to provide a sulfonated coumarin-based dye having an excitation spectrum maximum wavelength in a wavelength range of 475 nm or more, for example, in a wavelength range of 475 to 510

Solution to Problem

As a result of intensive studies to solve the above problems, the present inventors have found that an aminocoumarin compound having a specific structure can solve the above problems, and have completed the present invention.

That is, the aminocoumarin compound of the present invention has a structure represented by the following formula (1).

[Chemical formula 1]

(In formula (1), Rs each independently represent a hydrogen atom or a methyl group, Q represents a sulfur atom, an oxygen atom, or N—$R^1$, and $R^1$ represents a hydrogen atom or a methyl group.)

The aminocoumarin compound is an aminocoumarin compound in which Q in the above formula (1) is a sulfur atom, an oxygen atom, or N—$R^1$.

The aminocoumarin compound-containing resin particle of the present invention contains the aminocoumarin compound and a resin particle containing the aminocoumarin compound.

In the aminocoumarin compound-containing resin particle, the resin particle is preferably an amino resin particle.

The aminocoumarin compound-containing resin particle preferably has an excitation spectrum maximum wavelength of 475 to 510 nm and a fluorescence spectrum maximum wavelength of 510 to 540 nm.

Advantageous Effects of Invention

The aminocoumarin compound of the present invention is a fluorescent dye that has a longer excitation wavelength than a conventionally known sulfonated coumarin-based compound described in Patent Literature 1 or the like and is effectively excited at a wavelength of 475 nm or more, particularly at a wavelength around 500 nm. The aminocoumarin compound of the present invention is a fluorescent dye that is excited, for example, at a wavelength of 475 to 510 nm and can be observed in a green light emission region of 510 to 540 nm using the wavelength characteristic, and can be expected to be suitably utilized in immunostaining or the like.

BRIEF DESCRIPTION OF THE DRAWINGS

[0018.1]

DESCRIPTION OF EMBODIMENTS

The aminocoumarin compound of the present invention has a structure represented by the following formula (1).

[Chemical formula 2]

(In formula (1), 12 Rs each independently represent a hydrogen atom or a methyl group.)

In formula (1), Q represents a sulfur atom, an oxygen atom, or N—$R^1$. The $R^1$ represents a hydrogen atom or a methyl group. The aminocoumarin compound of the present invention has a benzothiazole structure when Q in formula (1) represents a sulfur atom. The aminocoumarin compound of the present invention has a benzoxazole structure when Q in formula (1) represents an oxygen atom. The aminocoumarin compound of the present invention has a benzimidazole structure when Q in formula (1) represents N—$R^1$.

The sulfonic acid group $SO_3H$ included in formula (1) may be bonded to any one of four bondable carbon atoms of the benzene ring contained in the benzothiazole structure, the benzoxazole structure, or the benzimidazole structure.

The aminocoumarin compound of the present invention has a different structure from a known sulfonated coumarin-based compound described in Patent Literature 1 or the like in that the nitrogen atom bonded to the coumarin structure forms two 6-membered rings with the four carbon atoms of the benzene ring contained in the coumarin structure, that is, the amino group of aminocoumarin has a julolidine structure.

The aminocoumarin compound of the present invention having such a structure has a longer excitation wavelength than a known sulfonated coumarin-based compound and an excitation spectrum maximum wavelength of 475 nm or more, for example, 475 to 510 mm. Furthermore, the aminocoumarin compound of the present invention has a longer light emission wavelength than a known sulfonated coumarin-based compound, and a fluorescence spectrum maximum wavelength of 510 nm or more, for example, 510 to 540 mm Here, the "excitation spectrum maximum wavelength" means a maximum wavelength in an excitation spectrum. The "fluorescent spectrum maximum wavelength" means a maximum wavelength in a fluorescence spectrum.

The aminocoumarin compound of the present invention represented by formula (1) is characterized by having a higher light emission intensity than an aminocoumarin compound formed by replacing the sulfone group of the aminocoumarin compound with a hydrogen atom.

The aminocoumarin compound of the present invention can be manufactured, for example, by a method for sulfonating a coumarin compound having a structure represented by the following formula (2). Specifically, by adding 1 ml of fuming sulfuric acid to 0.1 g of the coumarin compound represented by formula (2) and causing a reaction of the resulting mixture at 0 to 140° C. for one to eight hours, the aminocoumarin compound of the present invention can be manufactured.

[Chemical formula 3]

(2)

(R and Q in formula (2) have the same meanings as R and Q in formula (1), respectively)

The aminocoumarin compound-containing resin particle of the present invention contains the aminocoumarin compound and a resin particle containing the aminocoumarin compound. The aminocoumarin compound-containing resin particle of the present invention can be suitably used for immunostaining or the like.

The aminocoumarin compound contained in the resin particle is as described above.

The aminocoumarin compound-containing resin particle is not particularly limited as long as being able to contain an aminocoumarin compound but is preferably a thermosetting resin. Since the thermosetting resin has a three-dimensional network structure, a dye enclosed therein is hardly detached from the resin particle, and is suitable for immunostaining or the like. Examples of the thermosetting resin include a melamine resin, a urea resin, an aniline resin, a guanamine resin, a phenol resin, a xylene resin, and a furan resin. Among these resins, an amino resin such as a melamine resin or a urea resin is particularly preferable because of being able to more effectively suppress the detachment of the dye from the resin particle.

The amount of the aminocoumarin compound contained in the resin particle is not particularly limited, and only needs to be able to ensure detectable luminance when the aminocoumarin compound-containing resin particle is used for immunostaining.

The average particle diameter of the aminocoumarin compound-containing resin particles is not particularly limited, but is usually 40 to 500 nm, and preferably 50 to 200 nm when the aminocoumarin compound-containing resin particle is used for immunostaining. When the average particle diameter of the aminocoumarin compound-containing resin particles exceeds 500 nm, a problem in stainability may occur. When the average particle diameter of the aminocoumarin compound-containing resin particle is less than 40 nm, a problem in visibility may occur.

The average particle diameter is obtained by measuring particle diameters of about 1000 aminocoumarin compound-containing particles by SEM observation and calculating an average value thereof.

The aminocoumarin compound-containing resin particle of the present invention can be manufactured according to a known method for manufacturing a dye-containing resin particle.

For example, the aminocoumarin compound-containing resin particle of the present invention can be manufactured by polymerizing a monomer raw material for resin synthesis in the presence of an aminocoumarin compound. Specifically, a monomer raw material for resin synthesis is added to an aqueous solution containing an aminocoumarin compound and a surfactant, and the resulting mixture is vigorously stirred usually at 55 to 75° C., preferably 68 to 72° C. for about 10 minutes, preferably for 10 to 15 minutes. Thereafter, a polymerization initiator is added thereto, and the resulting mixture is vigorously stirred at 55 to 75° C., preferably 68 to 72° C. for four to 24 hours, preferably four to five hours to be subjected to emulsion polymerization. Furthermore, the liquid temperature is raised to 80 to 90° C., preferably 80 to 82° C., and the reaction solution is vigorously stirred for 30 to 60 minutes, preferably 30 to 40 minutes. The reaction solution is usually divided into aggregates and a particle dispersion which is a supernatant. The particle dispersion is collected from the reaction solution. The particle dispersion is centrifuged to remove the dispersion medium which is a supernatant, and then ultrapure water is added to the precipitate, followed by ultrasonic dispersion. The process including centrifugation, addition of ultrapure water to the precipitate, and ultrasonic dispersion are repeated several more times. As a result, an aqueous dispersion of aminocoumarin compound-containing resin particles is obtained.

The monomer raw material for resin synthesis is a raw material that can form the resin particle by polymerization.

The addition amount of the aminocoumarin compound is usually 1 to 50 mg with respect to 1 g of a monomer raw material for resin synthesis.

The surfactant is not particularly limited, and a surfactant used for a normal emulsion polymerization reaction can be used. As the surfactant, any one of anionic, nonionic, and cationic surfactants can be used. Examples of the anionic surfactant include sodium dodecylbenzene sulfonate. Examples of the nonionic surfactant include polyethylene glycol and polyoxyethylene alkyl ether. Examples of the cationic surfactant include dodecyltrimethylammonium bromide. The surfactant may be used singly or in combination of two or more kinds thereof.

Preferable examples of a commercially available surfactant include "Emulgen" (registered trademark, manufactured by Kao Corporation) and "Neopelex" (registered trademark, manufactured by Kao Corporation). An active ingredient of Emulgen is polyoxyethylene alkyl ether, and an active ingredient of Neopelex is sodium dodecylbenzene sulfonate.

The addition amount of a surfactant is usually 1 to 3 mg with respect to 1 g of a monomer raw material for resin synthesis.

Examples of the polymerization initiator include a thermal polymerization initiator such as an azo compound or a peroxide that generates a radical by heat. Preferable examples of the azo compound include 2,2'-azobis(2-methylpropionamidine) dihydrochloride (V-50). Preferable examples of the peroxide include ammonium persulfate. The polymerization initiator may be a redox polymerization initiator.

The addition amount of the polymerization initiator is usually 0.1 to 1.5 mg, and preferably 0.3 to 0.45 mg with respect to 1 g of a monomer raw material for resin synthesis.

In the aminocoumarin compound-containing resin particle, the resin particle is preferably an amino resin particle.

The aminocoumarin compound-containing resin particle preferably has an excitation spectrum maximum wavelength of 475 to 510 nm and a fluorescence spectrum maximum wavelength of 510 to 540 nm.

The aminocoumarin compound-containing resin particle of the present invention manufactured by incorporating the aminocoumarin compound represented by formula (1) into a resin tends to have a higher light emission intensity than an aminocoumarin compound-containing resin particle manufactured by incorporating an aminocoumarin compound formed by replacing the sulfone group of the aminocoumarin compound with a hydrogen atom into a resin. It is presumed that this is because the aminocoumarin compound represented by formula (1) is more easily contained in a resin than the aminocoumarin compound formed by replacing the sulfone group of the aminocoumarin compound with a hydrogen atom, and is taken in a resin in a larger amount.

The aminocoumarin compound and the aminocoumarin compound-containing resin particle of the present invention can be suitably used in immunostaining or the like because of having the above characteristics.

Specifically, when fluorescent labeling is performed by a fluorescent labeling method with the aminocoumarin compound-containing resin particle of the present invention, a green bright spot is clear. In a case of multiple labeling, leakage into another color region such as a red region is small, and a good balance between a green bright spot and a red bright spot is obtained.

Hereinafter, the fluorescent labeling method with the aminocoumarin compound-containing resin particle will be described.

Examples of the fluorescent labeling method include an immunostaining method and FISH. Specific operation methods of the immunostaining method and FISH are not particularly limited, and known methods can be used. In a conventional immunostaining method or FISH for performing labeling with a dye particle, it is only required to use the aminocoumarin compound-containing particle as the dye particle.

In a case of the immunostaining method, not only HER2 and Ki67 but also a staining target protein such as PDL1, CTLA4, CD8, CD30, CD48, or CD59 can be stained with the aminocoumarin compound-containing particle.

The fluorescent labeling method may be multiple labeling including labeling with the aminocoumarin compound-containing particle. That is, multiple labeling is performed on two or more labeling targets with different dyes, and at least one of the staining targets can be labeled with the aminocoumarin compound-containing particle. For example, as for a plurality of labeling targets, labeling is performed on some of the labeling targets with the aminocoumarin compound-containing particle, and labeling is performed on the other labeling targets with a particle containing a dye that emits light other than green light. Labeling can be performed on the plurality of labeling targets separately for green and colors other than green.

For example, in the immunostaining method, multiple staining is performed on at least two staining target proteins selected from PDL1, CTLA4, CD8, CD30, CD48, and CD59 with different dyes, and at least one of the staining target proteins can be stained with the aminocoumarin compound-containing particle. As a result, for example, PDL1 is stained with the aminocoumarin compound-containing particle in green, CTLA4 is stained in red, and PDL1 and CTLA4 can be labeled with different colors.

In this multiple staining, multiple staining is performed on at least two staining target proteins selected from the group consisting of PDL1, CTLA4, CD8, CD30, CD48, CD59, IDO, TDO, CSF-1R, HDAC, CXCR4, FLT-3, TIGIT, INF-α, INF-β, INF-ω, INF-ε, INF—K, INF-y, INF-λ, CSF, EPO, EGF, FGF, PDGF, HGF, TGF, CD3, CD4, CD25, CD28, CD80, CD86, CD160, CD57, OX40 (also known as CD134), OX40L (also known as CD252), ICOS (also known as CD278), ICOSL (also known as CD275), CD155, CD226, CD112, CD27, CD70, 4-1BB (also known as CD137), 4-1BBL (also known as CD137L), GITR (also known as CD357), GITRL, BTLA (also known as CD272), HVEM (also known as CD270), TIM-3, Galectin-9, LAG-3 (also known as CD223), B7-H3 (also known as CD276), B7-H4, B7-H5, CD40, CD40L, PD-1, PD-L2, 2B4 (also known as CD244), KLRG-1, E-Cadherin, N-Cadherin, R-Cadherin, CD68, CD163, and CSF1-R with different dyes, and at least one of the staining target proteins can be stained with the aminocoumarin compound-containing particle.

When labeling is performed with the aminocoumarin compound-containing particle, a clear green bright spot can be confirmed, and leakage into another color region such as a red region is small. For this reason, when green labeling is performed on a specific labeling target with the aminocoumarin compound-containing particle and red labeling is performed on the other staining targets with a dye particle containing a red dye, leakage of an obtained green bright spot into a red region is small, and a good balance between a green bright spot and a red bright spot is obtained.

The aminocoumarin compound has a light emission region closer to a red region than a coumarin compound other than the aminocoumarin compound. However, when labeling is performed with the aminocoumarin compound-containing particle, leakage into a red region is rather smaller than that of a dye particle containing a coumarin compound other than the aminocoumarin compound.

EXAMPLES

Example 1

In a 20 mL vial, 600 mg of compound (3) represented by the following formula (3) was put, 6 mL of fuming sulfuric acid was added thereto, and the resulting mixture was stirred at 25° C. for four hours to cause a reaction. Progress of the reaction was confirmed by TLC. Specifically, a part of the reaction solution was neutralized with a NaOH aqueous solution. Thereafter, ethanol was added to the reaction solution, and TLC was performed using a solution obtained by mixing CHCl$_3$ and MeOH at a ratio of 2:3. An Rf value of a target product was 0.73, while an Rf value of the raw material was 0.88. Convergence of the reaction and generation of the target product were confirmed from the data of TLC.

Ice was put in a 50 mL vial up to the height of about 80% (30 mL), and the reaction solution was put thereinto little by little. A suspension in which a generated dye was suspended was obtained. The suspension was centrifuged, and the supernatant was removed to collect the dye as a precipitate. The precipitate was dispersed in 10 mL of pure water. This dispersion was centrifuged, the supernatant was removed, and the precipitate was collected and dispersed again in 10 mL of pure water. This dispersion was centrifuged, the supernatant was removed, and the precipitate was collected. The collected precipitate was dispersed in ethanol. This dispersion was centrifuged, and the supernatant was removed to obtain an aminocoumarin compound I represented by the following formula (I) as a precipitate. The aminocoumarin compound I had a yield of 80%.

The obtained precipitate was dried. Thereafter, the obtained powder was added to pure water and then neutralized with a NaOH aqueous solution to dissolve the precipitate, and the pH of the solution was set to 7 to 8. This solution was dried with a lyophilizer to obtain a Na salt of the aminocoumarin compound I. It was confirmed that the aminocoumarin compound I was rapidly dissolved in water by forming the aminocoumarin compound I into a Na salt, while the aminocoumarin compound I had poor solubility in water in a form of a sulfonic acid.

The aminocoumarin compound I was dissolved in a solvent obtained by mixing redistilled water (DDW) and ethanol at a ratio of 10:1 to manufacture a 10 nM solution. For this solution, an excitation spectrum maximum wavelength, a fluorescence spectrum maximum wavelength, and a fluorescence intensity at an excitation wavelength of 490 nm were measured using a spectrofluorimeter F-7000 (manufactured by Hitachi, Ltd.). Table 1 illustrates results thereof. For an excitation spectrum, by fixing a fluorescence wavelength to be detected and scanning the wavelength of excitation light, a fluorescence intensity was measured. For a fluorescence spectrum, by fixing the wavelength of excitation light, a fluorescence intensity was measured.

The raw material before sulfonation and the present compound were subjected to 1H-NMR measurement to confirm that the target sulfonated product was obtained.

1H-NMR (400 MHz, CDCl3) (compound (3)) before sulfonation: δ=1.31 (s, 6H), 1.59 (s, 6H), 1.77 (t, 2H), 1.83 (t, 2H), 3.29 (t, 2H), 3.38 (t, 2H), 7.30 (s, 1H), 7.36 (t, 1H), 7.47 (t, 1H), 7.94 (d, 1H), 8.00 (d, 1H), 8.83 (s, 1H)

1H-NMR (400 MHz, CD3OD) (aminocoumarin compound I) after sulfonation: δ=1.37 (s, 6H), 1.59 (s, 6H), 1.83 (s broad, 2H), 1.89 (s broad, 2H), 3.52 (s broad, 2H), 3.61 (s broad, 2H), 7.46 (s, 1H), 7.95 (d, 1H), 8.11 (d, 1H), 8.53 (s, 1H), 8.69 (s, 1H))

[Chemical formula 4]

(3)

[Chemical formula 5]

(I)

Example 2

An aminocoumarin compound II represented by the following formula (II) was obtained by a similar method to Example 1 except that compound (4) represented by the following formula (4) was used instead of the compound represented by formula (3). The aminocoumarin compound II had a yield of 82%.

Using the aminocoumarin compound II, the excitation spectrum maximum wavelength, the fluorescence spectrum maximum wavelength, and the fluorescence intensity were measured in a similar manner to Example 1. Table 1 illustrates results thereof.

1H-NMR (400 MHz, CDCl3) (compound (4)) before sulfonation: δ=1.99 (m, 4H), 2.79 (t, 2H), 2.94 (t, 2H), 3.33 (s broad, 4H), 7.05 (s, 1H), 7.34 (t, 1H), 7.46 (t, 1H), 7.92 (d, 1H), 8.00 (d, 1H), 8.80 (s, 1H)

1H-NMR (400 MHz, CD3OD) (aminocoumarin compound II) after sulfonation: δ=1.95 (m, 4H), 2.78 (t, 2H), 2.84 (t, 2H), 3.36 (m, 4H), 7.20 (s, 1H), 7.89 (d, 1H), 7.94 (d, 1H), 8.38 (s, 1H), 8.80 (s, 1H)

[Chemical formula 6]

(4)

[Chemical formula 7]

(II)

Example 3

An aminocoumarin compound III represented by the following formula (III) was obtained by a similar method to Example 1 except that compound (5) represented by the following formula (5) was used instead of the compound represented by formula (3). The aminocoumarin compound III had a yield of 80%.

Using the aminocoumarin compound III, the excitation spectrum maximum wavelength and the fluorescence spectrum maximum wavelength were measured in a similar mariner to Example 1. Table 1 illustrates results thereof.

[Chemical formula 8]

(5)

[Chemical formula 9]

(III)

Example 4

An aminocoumarin compound IV represented by the following formula (IV) was obtained by a similar method to Example 1 except that compound (6) represented by the following formula (6) was used instead of the compound represented by formula (3). The aminocoumarin compound IV had a yield of 75%.

Using the aminocoumarin compound IV, the excitation spectrum maximum wavelength and the fluorescence spectrum maximum wavelength were measured in a similar mariner to Example 1. Table 1 illustrates results thereof.

1H-NMR (400 MHz, CDCl3) (compound (6)) before sulfonation: δ=1.98 (m, 4H), 2.78 (t, 2H), 2.93 (t, 2H), 3.33 (m, 4H), 6.98 (s, 1H), 7.30 (d, 1H), 7.31 (d, 1H), 7.57 (t, 1H), 7.78 (t, 1H), 8.50 (s, 1H)

1H-NMR (400 MHz, CD3OD) (aminocoumarin compound IV) after sulfonation: δ=1.97 (s broad, 4H), 2.80 (m, 2H), 2.87 (m, 2H), 3.39 (m, 4H), 7.19 (s, 1H), 7.72 (d, 1H), 7.87 (d, 1H), 8.05 (s, 1H), 8.65 (s, 1H)

[Chemical formula 10]

(6)

[Chemical formula 11]

(IV)

Example 5

An aminocoumarin compound V represented by the following formula (V) was obtained by a similar method to Example 1 except that compound (7) represented by the following formula (7) was used instead of the compound represented by formula (3). The aminocoumarin compound V had a yield of 70%.

Using the aminocoumarin compound V, the excitation spectrum maximum wavelength and the fluorescence spectrum maximum wavelength were measured in a similar mariner to Example 1. Table 1 illustrates results thereof.

1H-NMR (400 MHz, CDCl3) (compound (7)) before sulfonation: δ=1.98 (m, 4H), 2.78 (t, 2H), 2.93 (t, 2H), 3.33 (m, 4H), 6.98 (s, 1H), 7.30 (d, 1H), 7.31 (d, 1H), 7.57 (t, 1H), 7.78 (t, 1H), 8.50 (s, 1H)

1H-NMR (400 MHz, CD3SOCD3) (aminocoumarin compound V) after sulfonation: δ=1.97 (s broad, 4H), 2.80 (m, 2H), 2.87 (m, 2H), 3.39 (m, 4H), 7.19 (s, 1H), 7.72 (d, 1H), 7.87 (d, 1H), 8.05 (s, 1H), 8.65 (s, 1H)

[Chemical formula 12]

(7)

[Chemical formula 13]

(V)

Example 6

An aminocoumarin compound VI represented by the following formula (VI) was obtained by a similar method to Example 1 except that compound (8) represented by the following formula (8) was used instead of the compound represented by formula (3). The aminocoumarin compound VI had a yield of 75%.

Using the aminocoumarin compound VI, the excitation spectrum maximum wavelength and the fluorescence spectrum maximum wavelength were measured in a similar mariner to Example 1. Table 1 illustrates results thereof.

[Chemical formula 14]

(8)

[Chemical formula 15]

(VI)

COMPARATIVE EXAMPLE 1

The fluorescence intensity was measured in a similar manner to Example 1 except that an aminocoumarin compound i represented by the following formula (i) was used instead of the aminocoumarin compound I. Table 1 illustrates results thereof.

[Chemical formula 16]

(i)

COMPARATIVE EXAMPLE 2

An aminocoumarin compound ii represented by the following formula (ii) was obtained by a similar method to Example 1 except that the aminocoumarin compound i represented by the above formula (i) was used instead of the compound represented by formula (3).

Using the aminocoumarin compound ii, the excitation spectrum maximum wavelength, the fluorescence spectrum maximum wavelength, and the fluorescence intensity were measured in a similar manner to Example 1. Table 1 illustrates results thereof.

1H-NMR (400 MHz, CDC13) (aminocoumarin compound i) before sulfonation: σ 5=1.25 (t, 6H), 3.46 (q, 4H), 6.56 (s, 1H), 6.67 (d, 1H), 7.36 (t, 1H), 7.48 (m, 2H), 7.99 (d, 1H), 8.01 (d, 1H), 8.90 (s, 1H)

1H-NMR (400 MHz, CD3SOCD3) (aminocoumarin compound ii) after sulfonation: 5=1.67 (t, 6H), 3.51 (m, 4H), 6.68 (s, 1H), 6.86 (d, 1H), 7.41 (d, 1H), 7.78 (d, 1H), 7.91 (d, 1H), 8.30 (s, 1H), 9.03 (s, 1H)

[Chemical formula 17]

(ii)

COMPARATIVE EXAMPLE 3

An aminocoumarin compound iii represented by the following formula (iii) was obtained by a similar method to Example 1 except that compound (9) represented by the following formula (9) was used instead of the compound represented by formula (3).

Using the aminocoumarin compound iii, the excitation spectrum maximum wavelength and the fluorescence spectrum maximum wavelength were measured in a similar mariner to Example 1. Table 1 illustrates results thereof.

[Chemical formula 18]

(9)

(iii)

COMPARATIVE EXAMPLE 4

An aminocoumarin compound iv represented by the following formula (iv) was obtained by a similar method to Example 1 except that compound (10) represented by the following formula (10) was used instead of the compound represented by formula (3).

Using the aminocoumarin compound iv, the excitation spectrum maximum wavelength and the fluorescence spectrum maximum wavelength were measured in a similar manner to Example 1. Table 1 illustrates results thereof.

[Chemical formula 20]

(10)

(iv)

TABLE 1

|  | Aminocoumarin compound | Excitation spectrum maximum wavelength (nm) | Fluorescence spectrum maximum wavelength (nm) | Fluorescence intensity |
| --- | --- | --- | --- | --- |
| Example 1 | Aminocoumarin compound I | 485 | 530 | 430 |
| Example 2 | Aminocoumarin compound II | 490 | 531 | 420 |
| Example 3 | Aminocoumarin compound III | 475 | 517 | Not measured |
| Example 4 | Aminocoumarin compound IV | 475 | 517 | Not measured |
| Example 5 | Aminocoumarin compound V | 485 | 530 | Not measured |
| Example 6 | Aminocoumarin compound VI | 485 | 530 | Not measured |
| Comparative Example 1 | Aminocoumarin compound i | Not measured | Not measured | 110 |
| Comparative Example 2 | Aminocoumarin compound ii | 470 | 515 | 160 |
| Comparative Example 3 | Aminocoumarin compound iii | 460 | 505 | Not measured |
| Comparative Example 4 | Aminocoumarin compound iv | 470 | 515 | Not measured |

Example 7

14.4 mg of the aminocoumarin compound I was added to and dissolved in 22 mL of water. To this solution, 2 mL of a 5% aqueous solution of emulsion (registered trademark) 430 (polyoxyethylene oleyl ether, manufactured by Kao Corporation) of an emulsifier for emulsion polymerization was added.

The temperature of this solution was raised to 70° C. while the solution was stirred on a hot stirrer, and then 0.65 g of a melamine resin raw material Nikalac MX-035 (manufactured by Nippon Carbide Industries Co., Ltd.) was added to the solution. To this solution, 1000 μL of a 10% aqueous solution of dodecylbenzenesulfonic acid (manufactured by Kanto Chemical Co., Ltd.) was added as a reaction initiator. The resulting mixture was heated and stirred at 70° C. for 50 minutes. Thereafter, the temperature of the mixture was raised to 90° C., and the mixture was heated and stirred for 20 minutes. An aminocoumarin compound-containing resin particle I was obtained by the above operation.

The obtained dispersion of the aminocoumarin compound-containing resin particle I was washed with pure water to remove impurities such as excess resin raw materials and the aminocoumarin compound. Specifically, the dispersion was centrifuged at 20000 G for 15 minutes in a centrifuge (micro cooled centrifuge 3740 manufactured by Kubota Corporation), and the supernatant was removed. Thereafter, ultrapure water was added thereto, and the resulting mixture was irradiated with ultrasonic waves to be redispersed. An operation of centrifugation, removal of a supernatant, and redispersion in ultrapure water was repeated five times.

Figure 1:
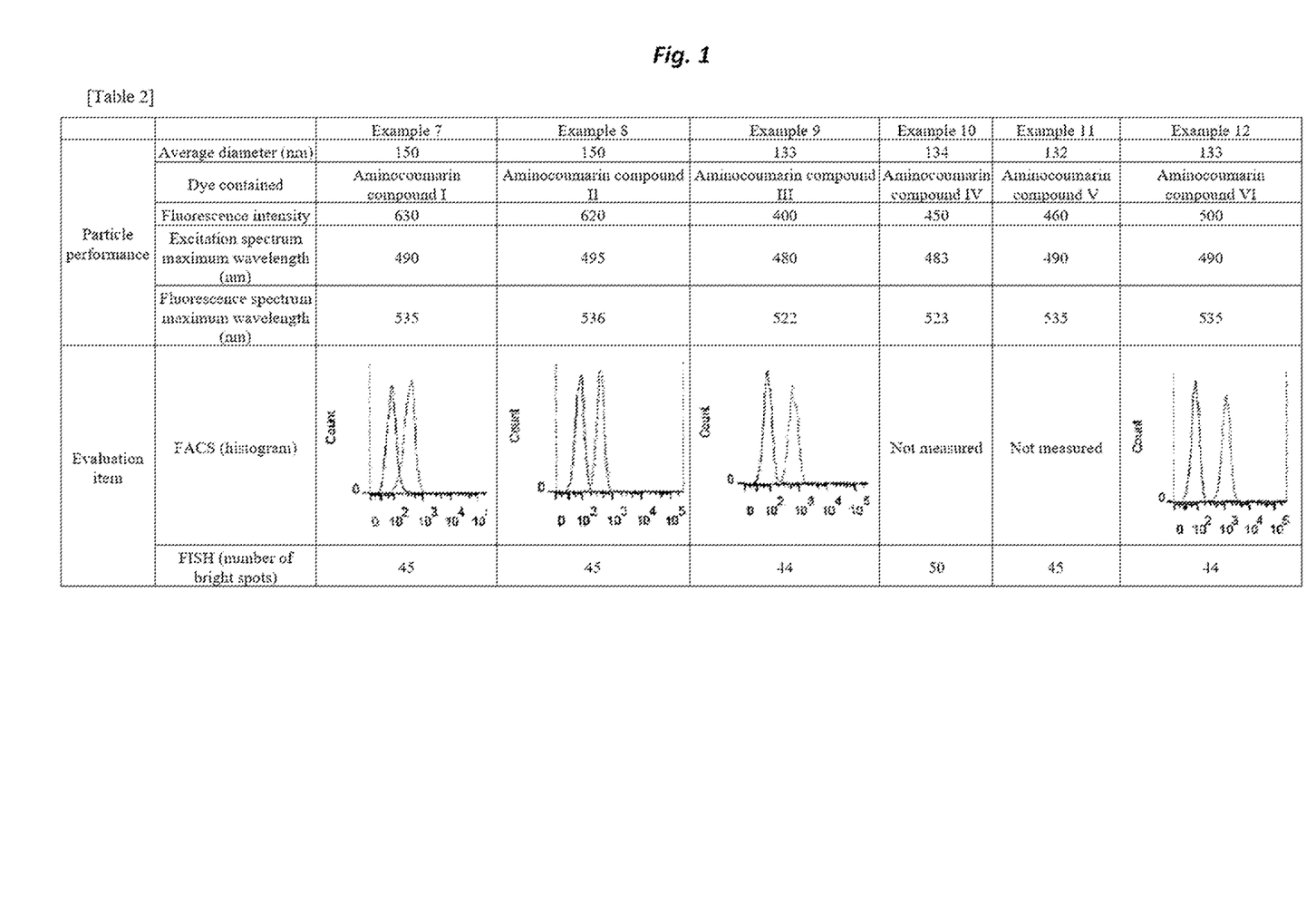
FIG. 1 illustrates Table 2 showing results of average particle diameter measurement, fluorescence intensity measurement, FACS, and FISH for aminocoumarin compound-containing resin particles I to VI.

The average particle diameter of the aminocoumarin compound-containing resin particles I was calculated from particle diameters in an SEM image. Table 2 in FIG. 1 illustrates results thereof.

The aminocoumarin compound-containing resin particles I were diluted to 0.0189 mg/mL, and 100 uL of the diluted solution was put in a fluorescence microcell. The fluorescence intensity thereof was measured at an excitation wavelength of 490 nm using a spectrofluorimeter F-7000 (manufactured by Hitachi, Ltd.). Table 2 illustrates results thereof.

The aminocoumarin compound-containing resin particles I were subjected to the following fluorescence activated cell sorting (FACS) and fluorescence in situ hybridization (FISH).

(FACS Evaluation)

Maleimide was introduced into an end of the aminocoumarin compound-containing resin particle I using an NHS-polyethylene glycol (PEG)-maleimide reagent, and a thiolated anti-HER2 antibody was bonded thereto.

Frozen cells of COL0201 obtained from American Type Culture Collection (ATCC) were melted in a thermostat bath at 37° C. Cells of about 1×10$^5$ cells/mL were suspended in a medium, and a first culture was performed in a 25 cm$^2$ flask. A culture solution in which the cells were increased to about 1×10$^6$ cells/mL was trypsinized, and some of cells removed from the flask were diluted with a Cell bunker solution (10% DMSO) and lyophilized to obtain stored cells. The remaining cells were passaged and cultured to a target amount of about 5×10$^7$, floated with a scraper, and collected, and some of the cells were used for FACS measurement.

The HER2 protein present on surfaces of the cultured cells was measured with FACSCalibur (trade name; manufactured by Becton, Dickinson and Company). A mixed solution of a PBS solution of the aminocoumarin compound-containing resin particles I and COLO201 cultured as described above was incubated at 4° C. for 30 minutes. 100 µl of the solution was put in a measuring tube, diluted to 2 ml by Assay Diluent (trade name, Becton, Dickinson and Company), and injected into FACSCalibur.

Table 2 illustrates results thereof. The graph illustrated as a result of FACS in Table 2 is a histogram in which the fluorescence intensity at 530 nm by 490 nm excitation light was plotted on the horizontal axis and the count number was plotted on the vertical axis. This graph indicates that as the histogram is shifted more to the right, a particle has a higher fluorescence intensity, that is, is brighter. In this graph, the result of Example 7 is illustrated in comparison with the result of Comparative Example 5 using the aminocoumarin compound-containing resin particle i described below. The same applies to the other Examples and Comparative Examples 6 to 8. The histogram having a peak around a fluorescence intensity of 90 is the histogram of Comparative Example 5, and the histogram having a peak around a fluorescence intensity of 500 is the histogram of Example 7. It is found that the histogram of Example 7 is significantly shifted to the right as compared with the histogram of Comparative Example 5. From this result, it is found that the aminocoumarin compound-containing resin particle I of Example 7 has a higher fluorescence intensity and is brighter than the aminocoumarin compound-containing resin particle i of Comparative Example 5.

(FISH Evaluation)

[Preparation of BAC Probe]

A nucleic acid molecules was prepared as follows according to a method described in CellBiochemBiophys. 2006; 45 (1) 59. For 1 µg (5 µL) of HER2-DNA clone (about 150 kbp) purchased from GSP, dTTP of the HER2-DNA clone (nucleic acid molecule) was replaced with DNP-labeled dUTP according to the protocol of a nick translation kit (product name "GSP-nick translation kit" K-015, manufactured by GSP) by a nick translation method as described below.

[Standard biotin labeling method by nick translation]

First, the following reagents were mixed in a centrifuge tube.

10× NickBuffer (Tris-HCl [pH 7.2], MgSO$_4$, DTT) . . . 2.5 µL

BSA (Nuclease-free BSA) . . . 1.5 µL dNTP mix (dATP, dCTP, and dCTP) . . . 5 µL dTTP . . . 0.5 µL, DNP-11-dUTP (product number NEL551001EA, manufactured by PerkinElmer Co., Ltd., 250 nmol/25 µL) . . . 0.15 µL Pure water (nuclease free water) . . . 3 µL Aqueous solution of 1 µg of the HER2-DNA clone (about 150 kbp) . . . 5 µL DNA Polymerase I (Tris-HCl [pH 7.5], EDTA, DTT, and glycerol) . . . 1 µL DNaseI . . . 5 µL Next, the mixture was reacted at 15° C. for four hours, and heated at 70° C. for 10 minutes to stop the reaction. After the reaction, 25 µL of distilled water was added to a centrifuge tube. The reaction solution of the biotin-labeled BAC probe was purified using a microspin column for purification of a nucleic acid ("Micro Spin S-200HR Column" manufactured by GE Healthcare, product number "#27-5120-01").

About 5.56 µL of a 3 M sodium acetate solution (pH 5.2) and 150 µL of 100% ethanol were added to this solution, and the resulting mixture was allowed to stand at −20° C. for one hour or more. The solution was centrifuged at 4° C. at 16000 rpm for 10 minutes to form a precipitate. Furthermore, 500 µL of 70% ethanol was added thereto. The resulting mixture was centrifuged at 4° C. at 16000 rpm for one minute, and the supernatant was removed. To the precipitate, 5 to 10 µL of distilled water was added to completely dissolve the precipitate, thus obtaining a solution of DNP-labeled BAC probe at a final concentration of 1 µg/250 µL.

[Preparation of DNA Probe in which Aminocoumarin Compound-Containing Resin Particle is Bonded to the BAC Probe]

An NHS-polyethylene glycol (PEG)-maleimide reagent was caused to react with a surface amino group of the aminocoumarin compound-containing resin particle I to introduce maleimide, and an anti-DNP antibody was bonded thereto.

A solution containing 25 µL (concentration 1 µg/250 µL) of the BAC probe labeled with DNP by nick translation and 1.0 µL (50 nmol/50 µL) of aminocoumarin compound-containing resin particles surface-modified with an anti-DNP antibody were mixed and subjected to a bonding reaction at room temperature for 30 minutes to obtain a DNA probe reagent for HER-2 detection.

[Storage of DNA Probe]

The DNA probe obtained as described above was diluted with a hybridization buffer (25% deionized formamide, 2×SSC, 200 ng/µL salmon sperm DNA, 5×Denhardt's solution, 50 mM sodium phosphate, pH 7.0, 1 mM EDTA) to a final concentration of 1 to 5 ng/µL. A free ligand was removed by an 5300 size spin column (Amersham Biosciences, Piscataway, N.J.) as needed. If the DNA probe was not used immediately, the DNA probe was stored in a frozen state at −20° C.

[Measurement of Copy Number of HER2 Genes]

The copy number of HER2 genes was measured by FISH. As described below, FISH was performed by performing a deparaffinization treatment, a pretreatment of a sample slide, an enzyme treatment, a sample fixing treatment, preparation of a probe, a sample slide DNA modification treatment, a hybridization treatment, a slide glass washing treatment, and a DAPI staining treatment in this order.

[Deparaffinization Treatment]

A deparaffinization treatment was performed by treating a sample slide of an HER2-positive stained control specimen ("HER2-FISH control slide Code PS-09006" manufactured by Pathology Research Institute Co., Ltd.) in the following order (1) to (4). (1) The sample slide is immersed in Hemo-De at normal temperature for 10 minutes. (2) The sample slide is immersed in fresh Hemo-De at normal temperature for 10 minutes. The same operation is repeated three times. (3) The sample slide is immersed in 100% ethanol for five minutes at normal temperature, washed twice, and dehydrated. (4) The sample slide is air-dried or dried on a slide warmer at 45 to 50° C.

[Pretreatment of sample slide]

In order to improve accessibility of the DNA probe, the sample slide was pretreated in the following order of (1) to (6) to remove proteins of a cell membrane and a nuclear membrane. (1) The sample slide is treated with 0.2 mol/L HCl at room temperature for 20 minutes. (2) The sample slide is immersed in purified water for three minutes. (3) The sample slide is immersed in a washing buffer (2×SSC: standard saline citrate) for three minutes. (4) The sample slide is immersed in a pretreatment solution (1 N NaSCN) at 80° C. for 30 minutes. (5) The sample slide is immersed in purified water for one minute. (6) The sample slide is immersed in a washing buffer (2×SSC) for five minutes, and this immersion operation is repeated twice.

[Enzyme Treatment]

The pretreated sample slide was subjected to the following treatments (1) to (4) in this order to be subjected to an enzyme treatment. (1) The pretreated sample slide is taken out. A lower end of the slide glass is attached to a paper towel to remove an excess washing buffer. (2) The sample slide is immersed in a protease solution heated to 37° C. for 10 to 60 minutes. This immersion treatment is desirably performed with 25 mg protease (37° C. for 60 minutes with 50 mL of 2500-3000 Units/mg) [pepsin]/1M NaCl [pH 2.0]) in order to degrade a cell membrane and a nuclear membrane protein, particularly collagen. (3) The sample slide is immersed in a washing buffer for five minutes. This operation is repeated twice. (4) The sample slide is air-dried or dried on a slide warmer at 45 to 50° C. for two to five minutes.

[Fixation of Sample]

The pretreated sample slide was subjected to the following treatments (1) to (3) as sample fixing treatments. (1) The sample slide is immersed in 10% neutral buffered formalin ("4% paraformaldehyde phosphate buffer" manufactured by Wako Pure Chemical Industries, Ltd., product number 163-20145) at normal temperature for 10 minutes. (2) The sample slide is immersed in a washing buffer for five minutes. The same operation as this operation is repeated twice. (3) The sample slide is air-dried or dried on a slide warmer at 45 to 50° C. for two to five minutes.

[Preparation of Probe]

The temperature of the solution of the DNA probe reagent that had been stored in a frozen state was returned to room temperature. The viscosity of the solution was sufficiently reduced to such an extent that a pipetting operation capable of collecting an accurate volume was possible, and the solution was mixed using a vortex mixer or the like.

[Denaturation of Sample Slide DNA]

As a denaturation treatment of DNA on the sample slide, the sample slide that had been subjected to the sample fixing treatment was subjected to the following treatments (1) to (8). (1) A wet box (airtight container with its side sealed with a paper towel) having a moistened paper towel laid on a bottom thereof before manufacturing a sample slide was put in a 37° C. incubator and preheated. (2) It is confirmed that the pH of a denaturing solution (70% formamide/SSC [150 mM NaCl, 15 mM sodium citrate]) is pH 7.0 to 8.0 at normal temperature. The denaturing solution is put in a Coplin jar and heated in a warm bath until the temperature of the solution is 72° C.±1° C. (put in in a warm bath at 72±1° C. for at least 30 minutes). (3) A hybridization area on the back of the sample slide is marked with a diamond pen or the like such that the hybridization area can be identified. (4) The sample slide is immersed in a Coplin jar containing a denaturing solution at 72±1° C. to denature DNA of the sample slide. (5) The sample slide is taken out from the denaturing solution using tweezers and immediately put in 70% ethanol at room temperature. The slide is shaken in order to remove formamide. The sample slide is immersed therein for one minute. (6) The sample slide is taken out from 70% ethanol, put in 85% ethanol, and shaken in order to remove formamide. The sample is immersed therein for one minute. The same operation is repeated twice with 100% ethanol. (7) A lower end of the sample slide glass is attached to a paper towel to remove ethanol, and the back of the slide glass is wiped with a paper towel. (8) The sample slide is air-dried with a dryer or dried with a slide warmer at 45 to 50° C. for two to five minutes.

[Hybridization]

The denatured sample slide was subjected to the following treatments (1) to (3) in this order, and was thereby subjected to a hybridization treatment using 10 µL (10 to 50 ng) of the DNA probe prepared as described above. (1) 10 µL of the prepared DNA probe was added to a hybridization area of the sample slide, and immediately the probe was covered with a 22 mm×22 mm cover glass to spread the probe uniformly. Air bubbles are prevented from entering the hybridization area. (2) The cover glass is sealed with paper bond. (3) The sample slide is put in a preheated wet box, covered with a lid, and is hybridized in a 37° C. incubator for 14 to 18 hours.

[Washing of Slide Glass]

The hybridized sample slide was subjected to the following treatments (1) to (6) in this order, and was thereby washed. (1) A post-hybridization washing buffer (2×SSC/0.3% NP-40) is put in a Coplin jar. The post-hybridization washing buffer is preheated to 72° C.±1° C. in a warm bath (put in a warm bath at 72° C.±1° C. for at least 30 minutes). (2) Another Coplin jar containing the post-hybridization washing buffer is prepared and maintained at room temperature. (3) The paper bond sealing is removed with tweezers. (4) The sample slide is put in the post-hybridization washing buffer. The cover glass is left until the cover glass is naturally peeled off in a solution. (5) The sample slide is taken out from the solution, an excess solution is removed, and the sample slide is immersed in the post-hybridization washing buffer heated to 72±1° C. for two minutes. Here, desirably, a temperature exceeding 73° C. is maintained for two minutes or less, and treatment is performed for two minutes or less. (6) The sample slide is taken out from the Coplin jar and air-dried under light shielding (for example, in a closed drawer or a closed cabinet shelf).

[DAPI Staining]

DAPI staining was performed as follows. First, 10 μL of a DAPI counterstain was added to a hybridization area of the sample slide. Next, the sample slide was hybridized, and then cell nuclei were stained by performing DAPI staining (2 μg/mL PBS) at 25° C. for 10 minutes in order to count the number of cells. The sample slide was covered with a cover glass and stored under light shielding until signal measurement. 4',6-diamidino-2-phenylindole,dihydrochloride (DAPI) manufactured by Molecular Probes (D1306) was used.

[Observation]

<Fluorescent Microscopic Observation>

For fluorescence microscopic observation, an HER2 gene stained tissue section was set in a fluorescence microscope Zeiss imager (Camera: MRm monochrome with cooling function, eye lens×10, objective lens×60 oil immersion, filter set HE46 manufactured by Zeiss (excitation filter 500 nm±12.5 nm, beam splitter 515 nm, fluorescence filter 535 nm±15 nm)). Fluorescence emission of an aminocoumarin compound-containing resin particle of the hybridized DNA probe was acquired as a fluorescence image (fluorescence still image).

Table 2 illustrates results of counting the number of bright spots from the obtained fluorescence image. There was a difference in the number of measured origin points because it was relatively difficult to find a green bright spot (signal) in a green background (noise) in Comparative Examples, while detection was possible without being affected by a noise because of a high luminance in Examples.

Examples 8 to 12

In Examples 8 to 12, the aminocoumarin compound-containing resin particles II to VI were manufactured by a similar method to Example 7 except that the aminocoumarin compounds II to VI were used, respectively, instead of the aminocoumarin compound I.

Average particle diameter measurement, fluorescence intensity measurement, FACS, and FISH were performed in a similar manner to Example 7 using the aminocoumarin compound-containing resin particles II to VI. However, in Examples 10 and 11, FACS was not performed. Table 2 illustrates results thereof.

COMPARATIVE EXAMPLES 5 TO 8

In Comparative Examples 5 to 8, the aminocoumarin compound-containing resin particles i to iv were manufactured by a similar method to Example 7 except that the aminocoumarin compounds i to iv were used, respectively, instead of the aminocoumarin compound I.

Figure 2:
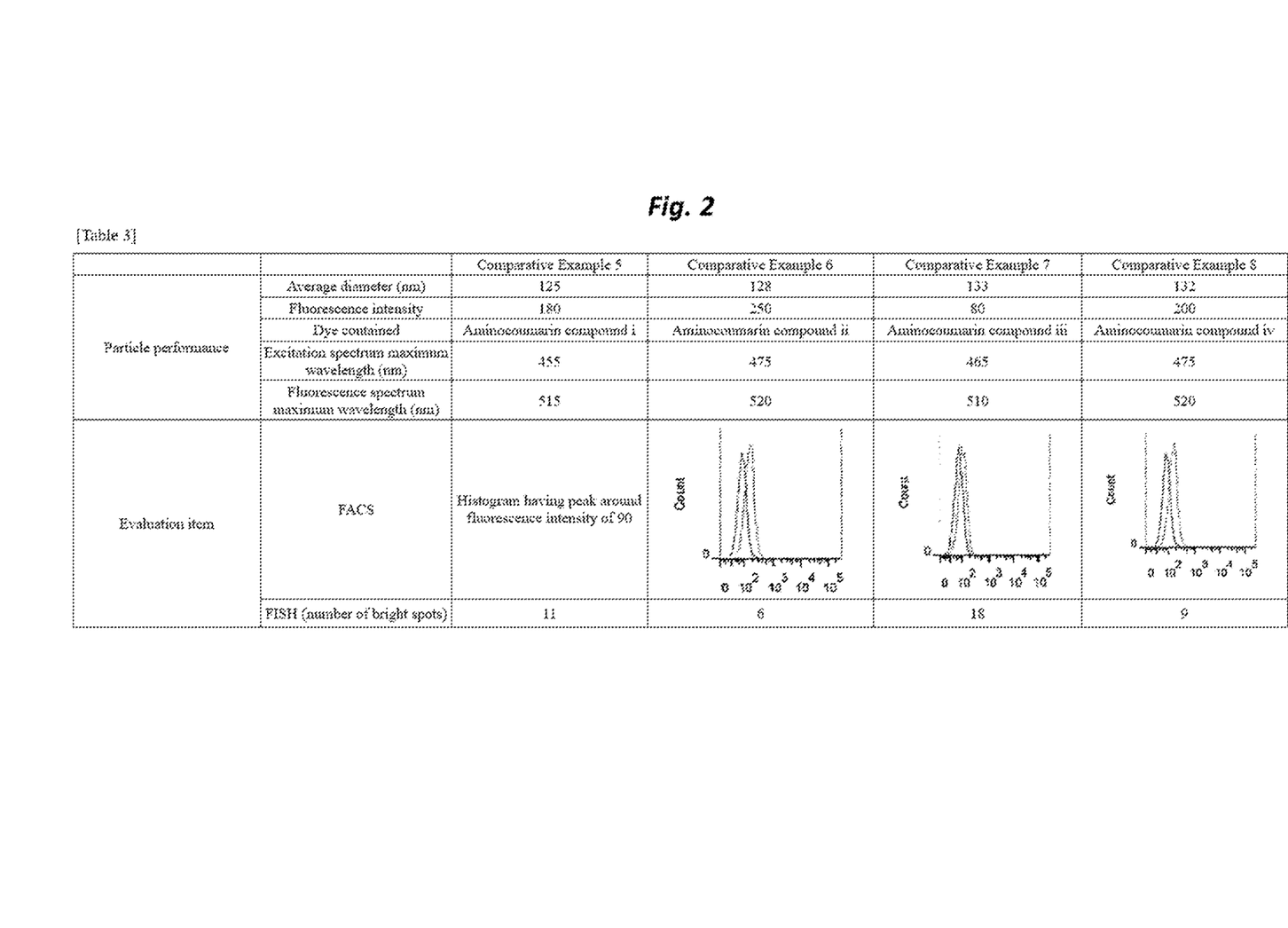
FIG. 2 illustrates Table 3 showing results of average particle diameter measurement, fluorescence intensity measurement, FACS, and FISH for aminocoumarin compound-containing resin particles i to iv.

Average particle diameter measurement, fluorescence intensity measurement, FACS, and FISH were performed in a similar manner to Example 7 using the aminocoumarin compound-containing resin particles i to iv. Table 3 in FIG. 2 illustrates results thereof. The results of FACS illustrated in Table 3 indicate that the histogram is not significantly shifted from the histogram of Comparative Example 5 despite of sulfonation of the fluorescent dye in Comparative Examples 6 to 8.

Example 13

0.1 mL of thionyl chloride was added to 3.4 mg of the aminocoumarin compound I, heated and mixed at 65° C. for four hours, and then vacuum dried to remove excess thionyl chloride. The obtained reaction product of the aminocoumarin compound and thionyl chloride was mixed with 3 μL of 3-aminopropyltrimethoxysilane (KBM 903 manufactured by Shin-Etsu Silicone Co., Ltd.) in 1.2 mL of N,N-dimethylformamide (DMF) to obtain an organoalkoxysilane compound.

0.3 mL of the obtained organoalkoxysilane compound solution was mixed with 24 mL of 99% ethanol, 0.3 mL of tetraethoxysilane (TEOS), 0.75 mL of ultrapure water, and 0.75 mL of 28% by mass ammonia water at 25° C. for three hours.

The mixture manufactured in the above steps was centrifuged at 10000 G for 20 minutes, and the supernatant was removed. To this precipitate, ethanol was added to disperse the precipitate, and rinsing to perform centrifugation was performed again. Furthermore, similar rinsing was repeated twice to obtain an aminocoumarin compound-containing particle VII. The 1000 obtained particles were observed with SEM, and an average particle diameter thereof was measured. The average particle diameter was 60 nm.

Example 14

An aminocoumarin compound-containing particle VIII was obtained by a similar method to Example 13 except that 0.85 mL of ultrapure water and 0.85 mL of ammonia water were used. The 1000 obtained particles were observed with SEM, and an average particle diameter thereof was measured. The average particle diameter was 80 nm.

Example 15

An aminocoumarin compound-containing particle IX was obtained by a similar method to Example 13 except that 1.10 mL of ultrapure water and 1.10 mL of ammonia water were used. The 1000 obtained particles were observed with SEM, and an average particle diameter thereof was measured. The average particle diameter was 150 nm.

The particle IX manufactured in Example 15 was subjected to fluorescence intensity measurement, FACS evaluation, and FISH evaluation to obtain results similar to those of Examples in Table 2.

Example 16

An aminocoumarin compound-containing particle X was obtained by a similar method to Example 13 except that 1.15 mL of ultrapure water and 1.15 mL of ammonia water were used. The 1000 obtained particles were observed with SEM, and an average particle diameter thereof was measured. The average particle diameter was 195 nm.

Example 17

An aminocoumarin compound-containing particle XI was obtained by a similar method to Example 13 except that 1.20 mL of ultrapure water and 1.20 mL of ammonia water were used. The 1000 obtained particles were observed with SEM, and an average particle diameter thereof was measured. The average particle diameter was 220 nm.

COMPARATIVE EXAMPLE 9

A dye-containing particle v was obtained by a similar method to Example 15 except that Pyrromethene 556 which is a green dye was used instead of the aminocoumarin compound I. The 1000 obtained particles were observed with SEM, and an average particle diameter thereof was measured. The average particle diameter was 150 nm.

COMPARATIVE EXAMPLE 10

A dye-containing particle vi was obtained by a similar method to Example 7 except that Pyrromethene 556 which is a green dye was used instead of the aminocoumarin compound I. The 1000 obtained particles were observed with SEM, and an average particle diameter thereof was measured. The average particle diameter was 150 nm.

COMPARATIVE EXAMPLE 11

A dye-containing particle vii was obtained by a similar method to Example 7 except that sulforhodamine 101 which is a red dye was used instead of the aminocoumarin compound I. The 1000 obtained particles were observed with SEM, and an average particle diameter thereof was measured. The average particle diameter was 150 nm.

Example 7A

Using the aminocoumarin compound-containing particle I manufactured in Example 7, immunostaining was performed by the following method.

(Streptavidin modification of dye-containing particle) The aminocoumarin compound-containing particle I was adjusted to 3 nM with phosphate buffered saline (PBS) containing 2 mM of ethylenediaminetetraacetic acid (EDTA). Succinimidyl-[(N-maleimidopropionamido)-dodecanethyleneglycol] ester (SM(PEG)$_{12}$, manufactured by Thermo Scientific Co., Ltd.) was mixed with this solution so as to have a final concentration of 10 mM, and a reaction was caused at 5° C. for one hour.

The mixture was centrifuged at 10000 G for 20 minutes, and the supernatant was removed. Thereafter, PBS containing 2 mM EDTA was added thereto to disperse the precipitate, and centrifugation was performed again. Washing was performed three times according to a similar procedure to obtain the aminocoumarin compound-containing particle I having a maleimide group attached to an end thereof.

To 210 μL of a borate buffer, 40 μL of streptavidin (manufactured by Wako Pure Chemical Industries, Ltd.) adjusted to 1 mg/mL was added, and then 70 μL of 2-iminothiolane hydrochloride (manufactured by Sigma Aldrich) adjusted to 64 mg/mL was added thereto to cause a reaction at room temperature for one hour. As a result, a thiol group (—NH—C(=NH$_2$$^+$Cl$^-$)—CH$_2$—CH$_2$—CH$_2$—SH) was introduced into an amino group of streptavidin.

The streptavidin solution was desalted with a gel filtration column (Zaba Spin Desalting Columns: Funakoshi) to obtain streptavidin that could be bonded to a silica-based particle. The total amount of the streptavidin (contained in an amount of 0.04 mg) was mixed with 740 μL of the silica-based particles adjusted to 0.67 nM using PBS containing 2 mM of EDTA, and a reaction was caused at room temperature for one hour.

10 mM of mercaptoethanol was added thereto, and the reaction was stopped. The obtained solution was concentrated using a centrifugal filter. Thereafter, unreacted streptavidin and the like were removed using a gel filtration column for purification to obtain the streptavidin-bonded aminocoumarin compound-containing particle I.

(Manufacture of Biotin-Modified Secondary Antibody)

In a 50 mM Tris-HCl solution (pH 7.5), 50 μg of an anti-rabbit IgG antibody was dissolved. The solution was mixed with a dithiothretol (DTT) solution so as to have a final concentration of 3 mM. Thereafter, the solution was caused to react at 37° C. for 30 minutes. Thereafter, a secondary antibody reduced with DTT was purified using a desalting column. 200 μL of the total amount of the purified antibody was dissolved in a 50 mM Tris-HCl solution (pH 7.5) to obtain an antibody solution. Meanwhile, a linker reagent "(+)-Biotin-PEG$_6$-NH-Mal" (manufactured by PurePEG, product number 2461006-250) having a spacer length of 30 angstroms was adjusted so as to have 0.4 mM using DMSO. 8.5 μL of this solution was added to the antibody solution, mixed, and caused to react at 37° C. for 30 minutes.

The reaction solution was supplied to a desalting column "Zeba Desalt Spin Columns" (manufactured by Thermo Scientific, Cat. #89882) to be purified. The absorption of the desalted reaction solution at a wavelength of 300 nm was measured with a spectrofluorometer ("F-7000" manufactured by Hitachi) to calculate the amount of protein contained in the reaction solution. The reaction solution was adjusted to 250 μg/mL with a 50 mM Tris solution, and the solution was used as a solution of a biotinylated secondary antibody.

(Staining)

(1) Specimen treatment step (1-1) Deparaffinization step

As a tissue section for staining, a tissue array slide of HER2 (3+) and HER2 (-) ("series of CB-A712" manufactured by Cosmo Bio Inc.) were used. The tissue array slide was deparaffinized.

(1-2) Activation Step

Washing was performed to replace the deparaffinized tissue array slide with water. The washed tissue array slide was subjected to an autoclave treatment in a 10 mM citrate buffer (pH 6.0) at 121° C. for 15 minutes to activate an antigen. The activated tissue array slide was washed with PBS, and the washed tissue array slide was blocked using PBS containing 1% BSA for one hour.

(2) Immunostaining Step (2-1) Primary Reaction

Using PBS containing 1% BSA, "anti-HER2 rabbit monoclonal antibody (4B5)" manufactured by Ventana was adjusted to 0.05 nM. The solution of the primary antibody was caused to react with the blocked tissue array slide at 4° C. overnight.

(2-2) Secondary Reaction

The tissue array slide that had been subjected to the primary reaction was washed with PBS, and then caused to react with the biotinylated secondary antibody diluted to 6 μg/mL with PBS containing 1% BSA at room temperature for 30 minutes.

(2-3) Fluorescent Labeling Treatment

The streptavidin-bonded aminocoumarin compound-containing particles I diluted to 0.02 nM with PBS containing 1% BSA were caused to react with the tissue array slide that had been subjected to the secondary reaction in a neutral pH environment (pH 6.9 to 7.4) at room temperature for three hours. The tissue array slide after the reaction was washed with PBS.

(3) Morphological Observation Staining Step

After immunostaining, hematoxylin and eosin staining (HE staining) was performed. An immunostained section was stained with a Mayer's hematoxylin solution for five minutes to be subjected to hematoxylin staining. Thereafter, the tissue section was washed with running water at 45° C. for three minutes. Next, the tissue section was stained with a 1% eosin solution for five minutes to be subjected to eosin staining.

(4) Fixing Step

The tissue section that had been subjected to the immunostaining step and the morphological observation staining step was immersed in pure ethanol for five minutes four times to be washed and dehydrated. Subsequently, the tissue section was immersed in xylene for five minutes four times to be cleared. Finally, the tissue section was enclosed using a mounting medium ("Entellan New" manufactured by Merck) to form a tissue array slide of an observation sample.

(5) Observation and measurement step

The tissue section that had been subjected to the fixing step was irradiated with predetermined excitation light to emit fluorescence. The tissue section in that state was observed and imaged using a fluorescence microscope ("BX-53" manufactured by Olympus Corp.) and a digital camera for microscope ("DP73" manufactured by Olympus Corp.). The wavelength (nm) of excitation light was caused to pass through an optical filter and was thereby set to 575 to 600 nm. Fluorescence to be observed was also caused to pass through an optical filter and was thereby set to a wavelength (nm) of 612 to 692 nm. As conditions of the excitation wavelength at the time of microscopic observation and image acquisition, irradiation energy around the center of a visual field was set to 900 W/cm$^2$ in excitation of 580 nm. Exposure time at the time of image acquisition was set arbitrarily (for example, set to 4000 ps) so as not to saturate the luminance of an image, and imaging was performed. The number of bright spots of the tissue of HER2 (3+) was taken as an average value of 1000 cells measured by an ImageJ FindMaxims method based on an image imaged at magnification of 400.

By measuring the number of bright spots S on a cell membrane in a visual field and the number of bright spots N outside a cell in the visual field, S/N was calculated. The S/N is illustrated in Table 4.

Examples 14a to 17A

In Examples 14A to 17A, immunostaining was performed by the following method using the aminocoumarin compound-containing particles VIII to XI manufactured in Examples 14 to 17, respectively.

(Streptavidin Modification of Dye-Containing Particle)

Streptavidin-bonded aminocoumarin compound-containing particles VIII to XI were obtained by a similar method to Example 7A except that the aminocoumarin compound-containing particles VIII to XI were used instead of the aminocoumarin compound-containing particle I, respectively.

(Manufacture of Biotin-Modified Secondary Antibody)

A solution of a biotinylated secondary antibody was obtained by a similar method to Example 7A.

(Staining)

S/N was calculated by a similar method to Example 7A except that the streptavidin-bonded aminocoumarin compound-containing particles VIII to XI were used instead of the streptavidin-bonded aminocoumarin compound-containing particle I. The S/N is illustrated in Table 4.

Example 8A

In Example 8A, using the aminocoumarin compound-containing particle II prepared in Example 8, immunostaining was performed by the following method.

(Streptavidin Modification of Dye-Containing Particle)

The streptavidin-bonded aminocoumarin compound-containing particle II was obtained by a similar method to Example 7A except that the aminocoumarin compound-containing particle II was used instead of the aminocoumarin compound-containing particle I.

(Manufacture of Biotin-Modified Secondary Antibody)

A solution of a biotinylated secondary antibody was obtained by a similar method to Example 7A.

(Staining)

(1) Specimen Treatment Step (1-1) Deparaffinization Step

A PDL1 tissue array slide was used as a tissue section for staining. The tissue array slide was deparaffinized.

(1-2) Activation Step

Washing was performed to replace the deparaffinized tissue array slide with water. The washed tissue array slide was subjected to an autoclave treatment in a 10 mM citrate buffer (pH 6.0) at 121° C. for 15 minutes to activate an antigen. The activated tissue array slide was washed with PBS, and the washed tissue array slide was blocked using PBS containing 1% BSA for one hour.

(2) Immunostaining Step (2-1) Primary Reaction

Using PBS containing 1% BSA, "anti-PD-L1 rabbit monoclonal antibody (E1L3N)" manufactured by Cell Signaling Technology was adjusted to 0.05 nM. The solution of the primary antibody was caused to react with the blocked tissue array slide at 4° C. overnight.

(2-2) Secondary Reaction

The tissue array slide that had been subjected to the primary reaction was washed with PBS, and then caused to react with the biotinylated secondary antibody diluted to 6 μg/mL with PBS containing 1% BSA at room temperature for 30 minutes.

(2-3) Fluorescent Labeling Treatment

The streptavidin-bonded aminocoumarin compound-containing particles II diluted to 0.02 nM with PBS containing 1% BSA were caused to react with the tissue array slide that had been subjected to the secondary reaction in a neutral pH environment (pH 6.9 to 7.4) at room temperature for three hours. The tissue array slide after the reaction was washed with PBS.

(3) Morphological Observation Staining Step

After immunostaining, hematoxylin and eosin staining (HE staining) was performed. An immunostained section was stained with a Mayer's hematoxylin solution for five minutes to be subjected to hematoxylin staining. Thereafter, the tissue section was washed with running water at 45° C. for three minutes. Next, the tissue section was stained with a 1% eosin solution for five minutes to be subjected to eosin staining.

(4) Fixing Step

The tissue section that had been subjected to the immunostaining step and the morphological observation staining step was immersed in pure ethanol for five minutes four times to be washed and dehydrated. Subsequently, the tissue section was immersed in xylene for five minutes four times to be cleared. Finally, the tissue section was enclosed using a mounting medium ("Entellan New" manufactured by Merck) to form a tissue array slide of an observation sample.

(5) Observation and Measurement Step

S/N was calculated by a similar method to Example 7A. The S/N is illustrated in Table 4.

COMPARATIVE EXAMPLE 9A-1

(Streptavidin Modification of Dye-Containing Particle)

A streptavidin-bonded dye-containing particle v was obtained by a similar method to Example 7A except that the dye-containing particle v was used instead of the aminocoumarin compound-containing particle I.

(Manufacture of Biotin-Modified Secondary Antibody)

A solution of a biotinylated secondary antibody was obtained by a similar method to Example 7A.

(Staining)

S/N was calculated by a similar method to Example 7A except that the streptavidin-bonded dye-containing particle v was used instead of the streptavidin-bonded aminocoumarin compound-containing particle I. The S/N is illustrated in Table 4.

COMPARATIVE EXAMPLE 9A-2

(Streptavidin Modification of Dye-Containing Particle)

The streptavidin-bonded dye-containing particle v was obtained by a similar method to Example 1 except that the dye-containing particle v was used instead of the aminocoumarin compound-containing particle I.

(Manufacture of Biotin-Modified Secondary Antibody)

A solution of a biotinylated secondary antibody was obtained by a similar method to Example 1.

(Staining)

S/N was calculated by a similar method to Example 8A except that the streptavidin-bonded dye-containing particle v was used instead of the streptavidin-bonded aminocoumarin compound-containing particle II. The S/N is illustrated in Table 4.

TABLE 4

| | Staining target | Dye | Type of particle | Particle diameter | S/N |
|---|---|---|---|---|---|
| Example 7A | HER2 | Aminocoumarin compound I | Silica | 60 | 120 |
| Example 14A | HER2 | Aminocoumarin compound I | Silica | 80 | 200 |
| Example 15A | HER2 | Aminocoumarin compound I | Silica | 150 | 205 |
| Example 16A | HER2 | Aminocoumarin compound I | Silica | 195 | 200 |
| Example 17A | HER2 | Aminocoumarin compound I | Silica | 220 | 105 |
| Example 8A | PDL1 | Aminocoumarin compound I | Silica | 150 | 120 |
| Comparative Example 9A-1 | HER2 | Pyrromethene 556 | Silica | 150 | 35 |
| Comparative Example 9A-2 | PDL1 | Pyrromethene 556 | Silica | 150 | 35 |

From Table 4, it was confirmed that S/N was improved by performing immunostaining using the aminocoumarin compound-containing particle containing the aminocoumarin compound I having a structure represented by formula (1) as compared with a case where a dye-containing particle containing Pyrromethene 556 as a dye other than the aminocoumarin compound having a structure represented by formula (1) was used.

Example 7B

Using the aminocoumarin compound-containing particle I manufactured in Example 7, multiple immunostaining of green and red was performed by the following method.

(Modification of Dye-Containing Particle)

Maleimide was introduced into an end of the aminocoumarin compound-containing resin particle I using an NHS-polyethylene glycol (PEG)-maleimide reagent, and a thiolated anti-HER2 antibody was bonded thereto to manufacture an anti-HER2 antibody-bonded aminocoumarin compound-containing resin particle.

In a similar manner to the above, maleimide was introduced into an end of the dye-containing particle vii, and a thiolated anti-Ki67 antibody was bonded thereto to manufacture an anti-Ki67 antibody-bonded dye-containing particle.

(Immunostaining of Tissue Specimen)

A human breast tissue specimen was subjected to immunostaining (IHC method) according to the following steps (1) to (13).

Step (1): A tissue specimen was immersed in a container containing xylene for 15 minutes. Xylene was changed twice during the procedure.

Step (2): The tissue specimen was immersed in a container containing ethanol for 10 minutes. Ethanol was changed twice during the procedure.

Step (3): The tissue specimen was immersed in a container containing water for 10 minutes.

Step (4): The tissue specimen was immersed in a 10 mM citrate buffer (pH 6.0).

Step (5): The tissue specimen was subjected to an autoclave treatment at 121° C. for five minutes.

Step (6): The tissue specimen after the autoclave treatment was immersed in a container containing PBS for 15 minutes. PBS was changed three times during the procedure.

Step (7): PBS containing 1% BSA was placed on the tissue specimen and allowed to stand for one hour.

Step (8): The anti-HER2 antibody-bonded aminocoumarin compound-containing resin particles adjusted to 0.1 nM with PBS containing 1% BSA were placed on the tissue specimen and allowed to stand overnight to label the tissue specimen with HER2.

Step (9): The labeled tissue specimen was immersed in a container containing PBS for 15 minutes.

Step (10): The anti-Ki67 antibody-bonded dye-containing particles adjusted to 0.1 nM with PBS containing 1% BSA were placed on the tissue specimen and allowed to stand overnight to label the tissue specimen with Ki67.

Step (11): The labeled tissue specimen was immersed in a container containing PBS for 30 minutes.

Step (12): The tissue specimen was fixed with a 4% neutral paraformaldehyde solution for 10 minutes, and then subjected to HE staining.

Step (13): Aquatex manufactured by Merck was dropped onto the tissue specimen. Thereafter, a cover glass was placed thereon, and the tissue specimen was enclosed.

(Microscopic Observation)

A fluorescence microscope manufactured by Carl Zeiss was used as a fluorescence microscope, and a filter set manufactured by Semrock was used as a filter set. As the filter set, the following two types corresponding to the immunostaining agents (for green and for red) were used.

TABLE 5

| Filter set | Excitation wavelength/light emission wavelength of filter set | |
|---|---|---|
| | For green | For red |
| Excitation filter | 470 nm (wavelength width 30 nm) | 586 nm (wavelength width 20 nm) |
| Beam splitter | 495 nm | 605 nm |
| Fluorescence filter | 525 nm (wavelength width 50 nm) | 628 nm (wavelength width 32 nm) |

The tissue specimen after immunostaining was placed on a stage. While the two types of filter sets for green and red were switched, the number of fluorescent bright spots of a fluorescence image of the tissue specimen was measured each time the filter sets were switched. Table 6 illustrates results thereof.

Example 8B

In Example 8B, multiple immunostaining was performed by a similar method to Example 7B except that the aminocoumarin compound-containing particle II was used instead of the aminocoumarin compound-containing resin particle VII. Table 6 illustrates results thereof.

COMPARATIVE EXAMPLE 10B

Multiple immunostaining was performed by a similar method to Example 7B except that the dye-containing particle vi was used instead of the aminocoumarin compound-containing resin particle VII. Table 6 illustrates results thereof.

TABLE 6

| | | Filter for green | | Filter for red | |
|---|---|---|---|---|---|
| | Green dye | Number of green bright spots | Number of red bright spots | Number of green bright spots | Number of red bright spots |
| Example 7B | Aminocoumarin compound I | 4100 | 24 | 30 | 1320 |
| Example 8B | Aminocoumarin compound II | 4200 | 36 | 30 | 1320 |
| Comparative Example 10B | Pyrromethene 556 | 1500 | 156 | 120 | 1300 |

From Table 6, as a result of double staining of HER2 and Ki67, it was confirmed that leakage of a green bright spot into a red bright spot was small by performing immunostaining using the aminocoumarin compound-containing particle containing the aminocoumarin compound I or II having a structure represented by formula (1) as compared with a case where a dye-containing particle containing Pyrromethene 556 as a dye other than the aminocoumarin compound having a structure represented by formula (1) was used.

Furthermore, it was confirmed from Table 6 that there was almost no influence on the number of red bright spots of double staining when immunostaining was performed using an aminocoumarin compound-containing particle containing the aminocoumarin compound I or II having a structure represented by formula (1).

The invention claimed is:

1. An aminocoumarin compound having a structure represented by the following formula (1):

(1)

wherein Rs each independently represent a hydrogen atom or a methyl group, Q represents a sulfur atom, an oxygen atom, or N—$R^1$, and $R^1$ represents a hydrogen atom or a methyl group.

2. The aminocoumarin compound according to claim 1, wherein Q in the formula (1) is a sulfur atom.

3. The aminocoumarin compound according to claim 1, wherein Q in the formula (1) is an oxygen atom.

4. The aminocoumarin compound according to claim 1, wherein Q in the formula (1) is N—$R^1$.

5. An aminocoumarin compound-containing resin particle comprising the aminocoumarin compound according to claim 1 and a resin particle containing the aminocoumarin compound.

6. The aminocoumarin compound-containing resin particle according to claim 5, wherein the resin particle is an amino resin particle.

7. The aminocoumarin compound-containing resin particle according to claim 5, having an excitation spectrum maximum wavelength of 475 to 510 nm and a fluorescence spectrum maximum wavelength of 510 to 540 nm.

8. The aminocoumarin compound-containing resin particle according to claim 6, having an excitation spectrum maximum wavelength of 475 to 510 nm and a fluorescence spectrum maximum wavelength of 510 to 540 nm.

* * * * *